United States Patent [19]

Carbone

[11] Patent Number: 5,658,350
[45] Date of Patent: *Aug. 19, 1997

[54] APPARATUS FOR CEMENTING INTRAMEDULLARY BONE PROSTHESIS

[75] Inventor: John J. Carbone, Baltimore, Md.

[73] Assignee: Dennis W. Lennox, Baltimore, Md.

[*] Notice: The term of this patent shall not extend beyond the expiration date of Pat. No. 5,340,362.

[21] Appl. No.: 202,899

[22] Filed: Feb. 28, 1994

Related U.S. Application Data

[63] Continuation of Ser. No. 777,726, Oct. 16, 1991, Pat. No. 5,340,362.
[51] Int. Cl.$^6$ ................................................. A61F 2/36
[52] U.S. Cl. ................................................. 623/23; 606/95
[58] Field of Search ................................. 623/16, 18, 23; 606/84, 95

[56] References Cited

U.S. PATENT DOCUMENTS

| 4,404,692 | 9/1983 | Eftekhar | 606/95 |
|---|---|---|---|
| 4,718,909 | 1/1988 | Brown | 623/16 |
| 4,892,550 | 1/1990 | Huebsch | 623/22 |
| 4,994,085 | 2/1991 | Sawai et al. | 623/23 |
| 5,041,141 | 8/1991 | Ypma et al. | 623/23 |
| 5,078,746 | 1/1992 | Garner | 623/16 |
| 5,340,362 | 8/1994 | Carbone | 623/23 |
| 5,376,123 | 12/1994 | Klaue et al. | 623/23 |

FOREIGN PATENT DOCUMENTS

| 0434604 | 11/1990 | European Pat. Off. | 623/23 |
|---|---|---|---|
| 4122950 | 1/1993 | Germany | 623/23 |
| 1424829 | 9/1988 | U.S.S.R. | 623/16 |

*Primary Examiner*—David H. Willse

[57] ABSTRACT

An intramedullary bone prosthesis to be rigidly cemented into position in the femur, and also applicable to total knee and shoulder replacement operations, is provided as an improved surgical technique. The prosthesis is composed of a femoral head base, a femoral head post, a long femoral stem, a cement canal along its longitudinal axis, a spacer, a collar, and a distal restrictor. The prosthesis is placed into the prepared medullary canal. With collar in position, a bone cement injector is readily threaded on to the proximal portion of the cement canal. Cement is injected and subsequently travels down through the canal, through the spacer, and eventually exits openings at the bottom of the spacer. The distal restrictor plug halts downward cement travel, thus initiating an upward, retrograde filling of the void in between the prosthesis and the cancellous bone wall. The cement reaches the collar or cement restrictor, thus proximally dislodging all air bubbles, blood, and blood products. Finally, during curing the cement is constantly and evenly pressurized by means of the cement injector, and excellent cement interdigitation is achieved.

5 Claims, 3 Drawing Sheets

APPARATUS FOR CEMENTING INTRAMEDULLARY BONE PROSTHESIS

BACKGROUND OF THE INVENTION

This invention relates to surgery and more particularly to the implanting of intramedullary bone prosthesis where an improved cementing technique may be utilized, especially in the femur. This application is a continuation of patent application Ser. No. 7/777,726, filed on Oct. 16, 1991, now U.S. Pat. No. 5,340,362.

BEST KNOWN PRIOR ART

The best known prior U.S. art is as follows:

| | | |
|---|---|---|
| 2,612,159 | 4,365,359 | 4,795,473 |
| 2,785,673 | 4,404,692 | 4,851,008 |
| 3,781,917 | 4,417,571 | 4,881,536 |
| 4,065,817 | 4,530,114 | 4,919,673 |
| 4,101,985 | 4,550,448 | 4,921,499 |
| 4,156,943 | 4,562,598 | 4,936,863 |
| 4,200,939 | 4,566,138 | 4,944,764 |
| 4,213,816 | 4,599,085 | 4,997,448 |
| 4,276,659 | 4,608,052 | 5,009,666 |
| 4,302,855 | 4,636,214 | 5,019,083 |
| 4,344,190 | 4,718,910 | 5,116,377 |
| 4,357,716 | 4,775,381 | 5,133,772 |
| EPO 434,604 | Ger. 3,704,089 | |

Femoral prosthesis operations may be broken down into two types: cement techniques and non-cement techniques. While both techniques have certain advantages and disadvantages, no one technique has proven to be ideal in the hip replacement category.

Both techniques involve amputating the femoral head at a designated point and preparing the medullary canal with some type of boring process. Non-cement techniques generally make use of a better prosthesis to medullary canal fit.

In the U.S. Pat. No. 2,612,159, Collison introduces a trochanteric plate which, when permanently placed on the femoral neck, can be joined to a femoral head. A similar scheme is proposed by Anderson in the U.S. Pat. No. 2,785,763 where the femoral head prosthesis is supported over a large area on the femoral neck.

The Kranz U.S. Pat. No. 4,562,598 teaches a prosthesis which is contoured to the medullary canal by means of an impervious prepreg member, while Mathys U.S. Pat. No. 3,781,917 discusses the anchoring of a femoral prosthesis through a screw placed through the collar of the prosthesis and into the outer corticalis.

In the U.S. Pat. No. 4,101,985, Baumann, et al teaches about a prosthesis with a special concave shape where small vibrations are taken care of by a threaded bolt attached to the prosthesis.

The Grimes U.S. Pat. No. 4,795,473 discloses a side plate device which results in an extramedullary prosthesis, while the Hofmann U.S. Pat. No. 4,936,836 shows a prosthesis which is enlarged for a tight fit after it has been introduced into the medullary canal.

U.S. Pat. No. 4,530,114, to Tepic, attempts to produce a prosthesis which seeks to emulate the characteristics of original bone stress absorption by using tension cables and a compression bolt.

The Kampen, et al U.S. Pat. No. 4,608,052 uses an integral attachment surface to let bone tissue grow into and thus better secure the prosthesis device. Similarly, Collier in U.S. Pat. No. 4,156,943 produces an orthopedic prosthesis which meets smoothness constraints of articulating bone joints yet contains pores ranging from 100 to 500 micrometers which are suitable for tissue growth.

Cementing techniques basically follow the same pattern. The medullary canal is prepared, a distal restrictor plug is inserted, cement is applied and pressurized, the prosthetic device is inserted, and the device is kept stationary until the cement has cured.

Some emphasis has been placed on developing better bone cements for these applications. The most typical and apparently effective bone cement is that composed of a polymethylmethacrylate polymer, usually liquid at temperatures above 45 degrees Celsius, but solid at body temperatures.

The Draenert U.S. Pat. No. 4,718,910 teaches a bone cement with a large surface provided to the implant but is characterized especially by exceptional mechanical strength. In the U.S. Pat. No. 4,200,939, Oser discusses a biocompatable, preformed, thermoplastic polymer other than the common polymethylmethacrylate type.

Intramedullary plugs of different varieties are used in cementing techniques. Emphasis is placed on obtaining a plug with the smallest chance of migration down the medullary canal. Migration leads to loss in cement pressurization and poor cement interdigitation. The Hardinge U.S. Pat. No. 4,276,659 discusses a hemispherical plug with radiating leaves. Similarly, the Lee, et al U.S. Pat. No. 4,344,190 introduces the concept of a biodegradable medullary plug which eventually disintegrates.

In the U.S. Pat. No. 4,302,855, an intramedullary plug which helps to position the prosthesis distally is introduced. A second intramedullary plug which aids in distal centering of a prosthesis, but which relies on penetration by the prosthesis, and which keeps the distal end of the prosthesis from being cemented is discussed by Filer in the U.S. Pat. 4,997,448. Distal centering by means of a cylindrical plug is referred to by Eftekhar in the U.S. Pat. No. 4,404,692. Van Syckle, et al teach in their U.S. Pat. No. 5,009,666 about a plug made for the purpose of filling avoid in a prosthesis and which insulates against cement penetration.

Agreed to by most orthopedic surgeons is the need for an even layer of bone cement in prosthesis operations. This is accomplished, as discussed by Nelson, et al in U.S. Pat. No. 4,417,571, by three spacers arranged in equilateral triangle position. A prosthesis device with spacers pre-attached is the subject of the U.S. Pat. No. 4,566,138 disclosed by Lewis, et al.

Prosthetic devices are often pre-coated before touching the cement bed in a medullary canal. The purpose of this is simply to provide a stronger bond for the cement and the prosthesis. The Morris U.S. Pat. No. 4,213,816 teaches the use of an interfacial layer or substrate formed between the underlying structural component and the porous layer. The porous layer is discussed by Rabb in U.S. Pat. No. 4,365,359, where the spraying or dipping into a polymethylmethacrylate substance is said to promote better tissue growth in the prosthesis.

The Kenna U.S. Pat. No. 4,550,448 discloses a porous coating composed of two layers of ball-shaped metallic particles which is suitable for tissue growth or cement applications. In the U.S. Pat. No. 4,599,085, Riess, et al teaches coating a prosthesis composed of a biocompatable metal and a particulate calcium phosphate ceramic with a layer of calcium phosphate.

Various cementing procedures have been developed to try to increase the interdigitation between the cement and its bonding surfaces. In the Noble, et al U.S. Pat. No. 4,881, 536, a preformed collar of bone cement is formed on the prosthesis which subsequently plunges down on the cement bed and forms adequate back pressure throughout the cement. The Homsy U.S. Pat. No. 4,636,214 teaches the use of a precisely formed medullary canal which minimizes the needed amount of cement.

In the U.S. Pat. No. 4,065,817, Branemark, et al discuss a prosthesis with a tubular support with lateral openings, where only the points having openings get cemented to the bone tissue, while the other points are left alone for the ingrowth of bone tissue, while the Willert, et al U.S. Pat. No. 4,919,673 teaches the use of a guiding rod, threaded on to the cavity of the prosthesis, to help position, implant, and set a bone prosthesis in a bed of cement. A device which allows the prosthesis to be prepositioned in the medullary cavity before the application of the cement is discussed in Brown in the U.S. Pat. No. 4,357,716.

Various other ideas and adjustments regarding prostheses have been previously discussed in the prior art. An adjustable prosthesis where the means of adjustment involves an inductive magnetic field is taught in the U.S. Pat. No. 4,921,499. Similarly, a prosthesis which is vibrated into position by means of ultrasonic sound is taught in the U.S. Pat. No. 5,091,083.

Stossel has modified a previous femoral prosthesis in the U.S. Pat. No. 4,944,764 to provide for a better leg abduction and to reduce the incision size for prosthesis fitting. A hip prosthesis which prevents fracture and can be used in conjunction with the medullary nailing technique is discussed in the U.S. Pat. No. 4,775,381. The Johnson U.S. Pat. No. 4,851,008 teaches of a prosthesis with an essentially stress free outer surface which has "T" shaped slots leading to a stress bearing subsurface.

OBJECTS OF THE INVENTION

It is an object of this invention to provide a novel method and apparatus for cementing an intramedullary bone prosthesis.

Another object of this invention is to provide a novel intramedullary bone prosthesis which may be permanently connected to a distal restrictor plug composed of compliant material capable of centering the distal tip and occluding intra meduilary canal.

Still another object of this invention is to provide an intramedullary bone prosthesis which can be threaded on to a bone cement injector.

To eliminate all air bubbles, blood and blood products by filling the void of cavity in a retrograde fashion is another object of this invention.

To constantly pressurize the cement as it is curing to ensure better interdigitation into the prosthesis and the adjacent cancellous bone wall, is still another object of this invention.

To eliminate the disaster of having a bone cement cure too quickly to properly position the prosthesis, is a further object of this invention.

To help control the toxic fumes emitted from a bone cement in the operating room, is another object of this invention.

And to provide an intra medullary bone prosthesis which is centered distally by means of a distal restrictor plug and proximally by means of at least one shim positioned in the critical zone is yet another object of this invention.

BRIEF DESCRIPTION OF THE DRAWINGS

These and other objects and attendant advantages of this invention will become more obvious and apparent from the following detailed specification and accompanying drawings in which.

DESCRIPTION OF THE PREFERRED EMBODIMENTS OF THE INVENTION

Figures 1A, 1B, 1C:
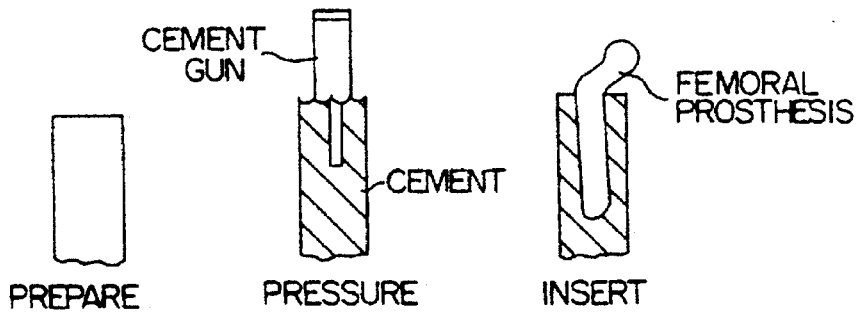
FIGS. 1a, 1b, and 1c are schematics of the steps in the conventional way of inserting and cementing a prosthesis in a bone structure.

Referring generally to FIGS. 1a, 1b, and 1c, there is shown schematically the conventional procedure for inserting and cementing a prosthesis in a bone cavity, with the bone structure first being prepared with the cavity, the prosthesis then is inserted in the cement.

Figures 2A, 2B, 2C:
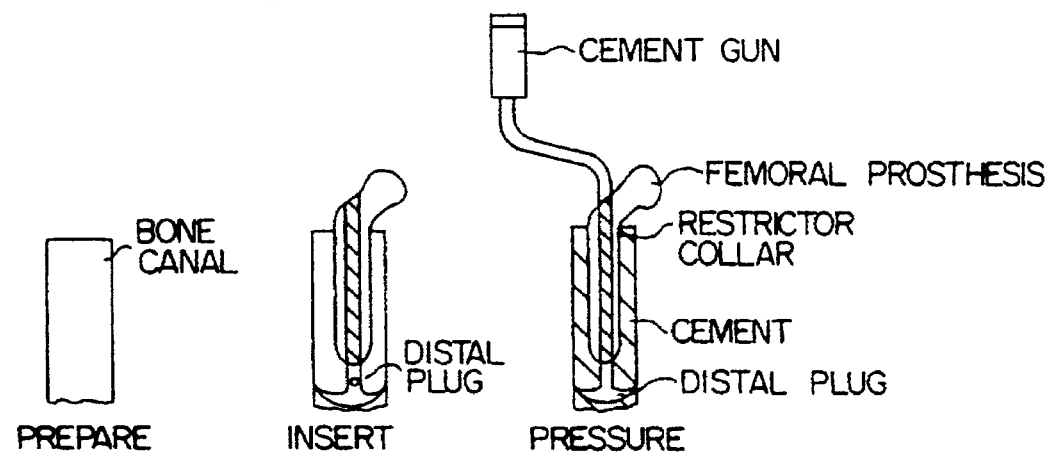
FIGS. 2a, 2b, and 2c, illustrate schematics of the steps of the novel way of this invention of inserting and cementing a prosthesis incorporating novel features of this invention.
Figure 3:
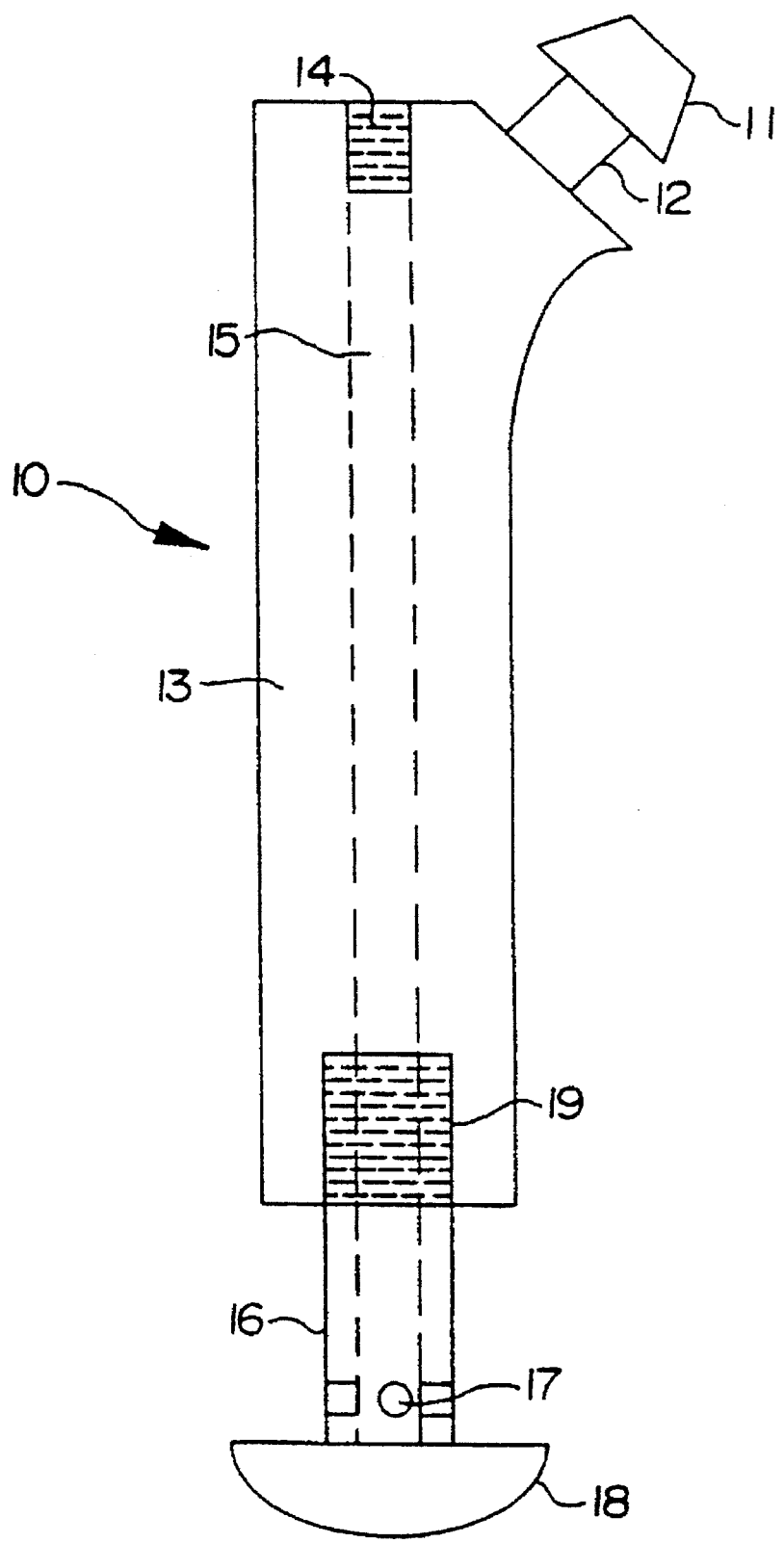
FIG. 3 is a front view of an intramedullary femoral bone prosthesis incorporating novel features of this invention.

In this invention, as shown in FIGS. 2a, 2b, and 2c, the bone structure is prepared with a cavity, the prosthesis is then inserted in the bone cavity, and the cement is passed through a canal in the prosthesis. This cement is then exited from the opposite end of the canal in a retrograde fashion into the cavity to subsequently fill it. A pressure collar is placed over the near end of the canal.

Figure 4:
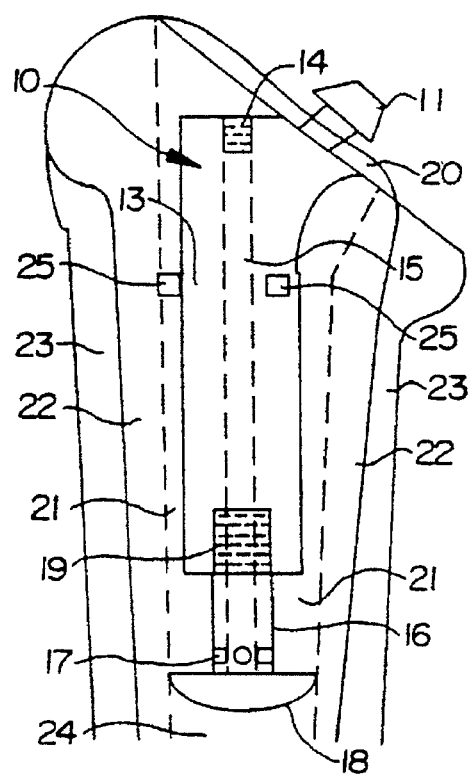
FIG. 4 is a front view of the intramedullary femoral bone prosthesis positioned for cementing inside the femur.
Figure 5:
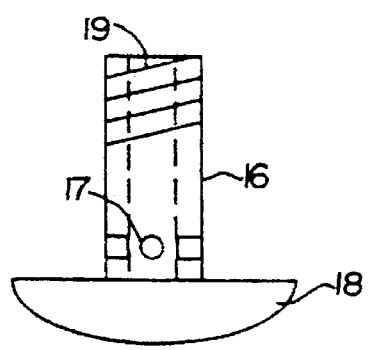
FIG. 5 is an enlarged front view of a spacer and distal restrictor plug of the intramedullary femoral bone prosthesis of FIG. 3.
Figure 6:
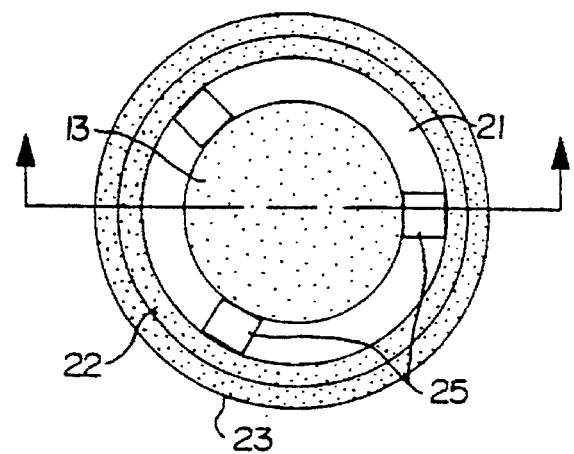
FIG. 6 is a cross sectional view of the intramedullary femoral bone prosthesis of FIG. 3 proximally centered into position by means of a plurality of shims.

Referring now to FIGS. 2a, 2b, 2c, and 3 to 6 of the drawings, there is shown the preferred embodiment of the invention showing a femoral intramedullary bone prosthesis 10 as well as its position inside a medullary canal 24 (FIG. 4).

The femoral intramedullary bone prosthesis 10 consists of a femoral head base 11, a femoral head post 12, a femoral stem 13, and a distal plug 18 composed of ,polymethylmethacrylate or conventional plugs now in use. The distal plug 18 is joined to a spacer 16 composed of polymethylmethacrylate or suitable material having a modulus of elasticity similar to that of bone cement.

The distal plug 18 and spacer 16 are fixed to the femoral stem 13 by means of a set of threads 19. As bone cement is filled in, the possibility of distal plug 18 migration down the medullary canal 24 is eliminated and a predetermined space is kept between the femoral stem 13 and the distal plug 18.

Positioning the femoral intramedullary bone prosthesis 10 begins with joining it to a collar or cement restrictor 20 shown in FIG. 2. The collar 20 encompasses the entire mouth of the opening of the medullary canal 24 while slightly overlapping a neighboring cancellous bone 22 and possibly a dense cortical bone 23. The femoral intramedullary bone prosthesis 10 is then placed inside the prepared medullary canal 24.

Equal spacing between the femoral stem 13 and the wall of the cancellous bone 22 is achieved at the distal end by means of automatic centering in the distal plug 18. At the proximal end, this spacing is achieved by means of at least one cement shim 25 each of predetermined thickness and placed around the cancellous bone wall 22 in polygonal configuration. The placement of shim is shown in FIG. 4.

Once positioned the femoral intramedullary bone prosthesis 10 is ready to receive the polymethylmethacrylate bone cement. Bone cement application begins by mating the threads on a bone cement injector to the threads 14 on the femoral stem canal 15. Once attached, bone cement is pushed down the femoral stem canal 15 until it reaches the top of the distal plug 18.

The bone cement then exits the femoral stem canal 15 through a plurality of openings 17 at the bottom of the spacer 16. In a retrograde manner, the bone cement works its way up the open cavity 21, blood, blood products and air bubbles are driven proximally and out of the medullary canal 24. As the bone cement fills the entire cavity 21, subsequent pressurization from the injecting device is added in a constant fashion, thus resulting in superior interdigitation of the cement to the femoral intramedullary bone prosthesis 10 and to the wall of the cancellous bone 22.

Obviously, many modifications and variations of the present invention are possible in light of the above description. It is therefore understood that within the scope of the appended claims the invention may be practiced otherwise than as specifically described.

What is claimed is:

1. A femoral intramedullary bone prosthesis for being rigidly cemented into position in a prepared medullary cavity, comprising:

a femoral head base located at one end of said bone prosthesis;

a femoral head post connected to said femoral head base;

a femoral stem having a proximal end connected to said femoral head post and a distal end;

a separate spacer means connected to said distal end of said femoral stem and having a bottom portion with at least one aperture therein;

a canal extending through said prosthesis from said proximal end of said femoral stem to said bottom portion of said spacer means, said canal communicating with said at least one aperture to allow cement to be supplied to said canal from said proximal end of said femoral stem to fill the prepared medullary canal through said aperture; and a distal restrictor plug joined to said bottom portion of said separate spacer means.

2. A femoral intramedullary bone prosthesis to be rigidly cemented into position in a prepared medullary canal as recited in claim 1, wherein said separate spacer means is formed of polymethylmethacrylate in order that the bone cement and said separate spacer means can form a cement mantle beneath said distal end of said femoral stem.

3. A femoral intramedullary bone prosthesis to be rigidly cemented into position in a prepared medullary cavity as recited in claim 1, wherein said separate spacer means is formed of a suitable material having a modulus of elasticity similar to that of the bone cement in order that said separate spacer means and the bone cement can form a cement mantle beneath said distal tip of said femoral stem.

4. A femoral intramedullary bone prosthesis to be rigidly cemented into position in a prepared medullary canal as recited in claim 1, wherein said distal restrictor plug is adapted to form a seal for preventing the bone cement from travelling past said distal restrictor plug along the medullary canal.

5. A femoral intramedullary bone prosthesis to be rigidly cemented in position in a prepared medullary canal as recited in claim 1, in combination with a bone cement injector, wherein a portion of said canal of said prosthesis is threaded adjacent said proximal end of said femoral stem, and said bone cement injector is joined to said threaded portion of said canal.

* * * * *